United States Patent [19]

Bernardi et al.

[11] 4,132,721

[45] Jan. 2, 1979

[54] OPTICALLY ACTIVE ANTHRACYCLINONES AND PROCESS THEREFOR

[75] Inventors: Luigi Bernardi; Pietro Giardino; Bianca Patelli, all of Milan; Federico Arcamone, Nerviano, Milan, all of Italy

[73] Assignee: Societa Farmaceutici Italia S.p.A., Milan, Italy

[21] Appl. No.: 802,789

[22] Filed: Jun. 2, 1977

[30] Foreign Application Priority Data

Jun. 19, 1976 [GB] United Kingdom ............... 25517/76

[51] Int. Cl.$^2$ ............................................. C07C 49/70
[52] U.S. Cl. ................................................... 260/365
[58] Field of Search ......................................... 260/365

[56] References Cited

U.S. PATENT DOCUMENTS

| | | | |
|---|---|---|---|
| 3,201,424 | 8/1965 | McCormick et al. ................ | 260/365 |
| 3,963,760 | 6/1976 | Bernardi et al. ..................... | 260/365 |
| 4,012,448 | 3/1977 | Smith et al. ......................... | 260/365 |
| 4,070,382 | 1/1978 | Kende et al. ......................... | 260/365 |
| 4,077,988 | 3/1978 | Arcamone et al. ................... | 260/365 |

OTHER PUBLICATIONS

*Chemical Abstracts,* vol. 85, No. 19-20, 1/22/75, abstract no. 14 2918j, Faubl, Hermann.
*Canadian Jol. of Chem.,* vol. 49, No. 16 (Sep. 1971), pp. 2712–2718, "Synthetic Studies of Hydronapthacenic Antibiotics, I. The Synthesis of 4–Demethoxy-7-O-methyl Daunomycinone", Wong et al.
*Canadian Jol. of Chem.,* vol. 55 (1973), pp. 466–467, "The Total Synthesis of Daunomycinone" Wong et al.

*Primary Examiner*—Allen B. Curtis
*Assistant Examiner*—Raymond Covington
*Attorney, Agent, or Firm*—Hubbell, Cohen, Stiefel & Gross

[57] ABSTRACT

Optically active anthracyclinones are prepared by reacting an optically active (−) 1,4-dimethoxy-6-hydroxy-6-acetyl-tetralin with a phthalic anhydride in the presence of AlCl$_3$ or AlBr$_3$ and an alkali metal chloride at 130–180° C. for 1 to 10 minutes.

9 Claims, No Drawings

OPTICALLY ACTIVE ANTHRACYCLINONES AND PROCESS THEREFOR

BACKGROUND OF THE INVENTION

This invention relates to a process for the synthesis of optically active anthracyclinones of the formula III:

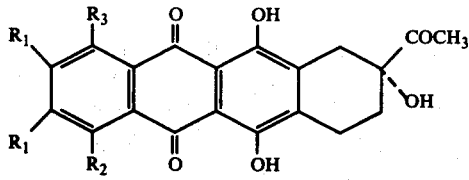

which compounds are key intermediates from which compounds of the formula I:

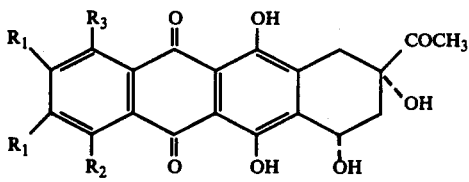

wherein:

(a) $R_1$ is hydrogen and $R_2$ and $R_3$ are the same and are both hydrogen or methyl, methoxy, chlorine or bromine;

(b) $R_2$ and $R_3$ are both hydrogen and $R_1$ is methyl, methoxy, chlorine or bromine; and (c) $R_1$ and $R_3$ are both hydrogen and $R_2$ is methoxy are obtained. These compounds of formula I can be obtained, for example, by bromination of the corresponding compound of formula III in the 7-position, followed by hydrolysis (A. S. Kende et al. J. Amer. Chem. Soc., 1976, 98, 1967).

Compounds of the Formula I, when condensed with (−)daunosamine give rise to glycosidic compounds which have shown therapeutic activity in the treatment of human and animal tumors. (See co-pending application, Ser. No. 579,901, now U.S. Pat. No. 4,046,878.)

The condensation of hydroquinone with phthalic anhydride in the presence of $AlCl_3$—NaCl at 240° C. to give quinizarin has been reported (Chem. Ber., 1929, 62, 512). Similarly, the condensation of phthalic anhydrides with substituted hydroquinones in the presence of $AlCl_3$—NaCl at 200° C. for two hours to give dihydroxyanthraquinones has been reported (Chem. Ber., 1963, 96, 2407). The literature is, however, silent concerning the possibility of a reaction between a phthalic anhydride and the less reactive 1,4-dialkoxybenzenes.

SUMMARY OF THE INVENTION

According to the invention, it has now surprisingly been found that an optically active (−) 1,4-dimethoxy-6-hydroxy-6-acetyl-tetralin of the formula II:

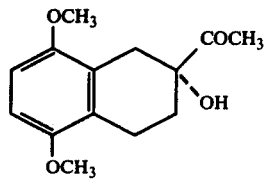

can be condensed in very high yield with a phthalic anhydride of the formula IV;

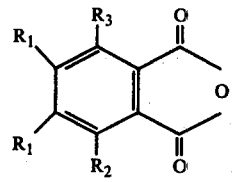

in the presence of aluminum chloride or bromide, preferably also in the presence of a chloride of an alkali metal, for example, LiCl, NaCl or KCl at from 130 to 180° C. After only 1 to 10 minutes, an anthracyclinone of the formula III is obtained directly. In spite of the high temperature and the strongly acidic conditions, the sensitive hydroxyketone side chain is retained and little if any dehydration product of the formula V:

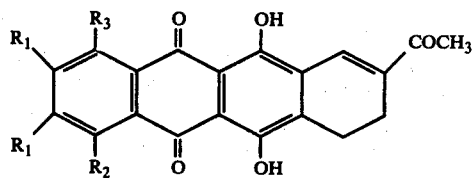

is formed although it is thermodynamically more stable than compounds of the formula III. However, the most unexpected and intriguing aspect of this reaction is the preservation of the chiral center: i.e., starting from an optically active tetralin II, an optically pure compound III is obtained, notwithstanding the high temperature and the strongly acidic conditions favoring the formation of a transient carbo-cation, which being planar, would necessarily yield a racemic molecule (Eliel, Stereo-chemistry of Carbon Compounds, page 36 and 372 — McGraw Hill, (1962).

The novel compounds of the formula III are also within the scope of the present invention.

DESCRIPTION OF THE PREFERRED EMBODIMENTS

The invention will now be illustrated in more detail by the following Examples:

EXAMPLE 1

4-demethoxy-7-desoxydaunomycinone (III): $R_1=R_2=R_3=H$)

An intimate mixture of 20 g. of aluminum chloride, 2 g. of sodium chloride, 2 g. of phthalic anhydride and 2 g. of (−) 1,4-dimethoxy-6-hydroxy-6-acetyl-tetralin (II) is introduced into a flask pre-heated on an oil bath at 170° C. The melt is poured into ice-water containing 100 g. of oxalic acid. The red solid thereby obtained is filtered and crystallized from diethyl ether to give 1.1 g. of 4-demethoxy-7-desoxydaunomycinone, m.p. 210–212° C., $[\alpha]_D^{20} = -84°$ (c=0.1 in chloroform). Electronic spectrum: λ max 256, 460, 486, 520 nm.

EXAMPLE 2

1,4-dimethyl-4-demethoxy-7-desoxydaunomycinone (III: $R_1=H$; $R_2=R_3=CH_3$)

Operating as in Example 1, using, however, 3,6-dimethylphthalic anhydride in place of phthalic anhydride and keeping the melt at 180° C. for 10 minutes, 0.7 g. of 1,4-dimethyl-4-demethoxy-7-desoxydaunomycinone m.p. 200–203° C.; $[\alpha]_D^{20} = -78°$ (c=0.1 in chloroform) is obtained. Electronic spectrum: λ 256, 472, 495, 530 nm.

EXAMPLE 3

2,3-dimethyl-4-demethoxy-7-desoxydaunomycinone
(III: $R_2=R_3=H$; $R_1=CH_3$)

Operating as in Example 1, using, however, 4,5-dimethylphthalic anhydride in place of phthalic anhydride and keeping the melt at 170° C. for 3 minutes, 1 g. of 2,3-dimethyl-4-demethoxy-7-desoxydaunomycinone, m.p. 228–230° C.; $[\alpha]_D^{20} = -87°$ (c=0.1 in chloroform) is obtained. Electronic spectrum: λ max 268, 458, 485, 528 nm.

EXAMPLE 4

1,4-dichloro-4-demethoxy-7-desoxydaunomycinone
(III: $R_1=H$; $R_2=R_3=Cl$)

Operating as in Example 2, but employing 3,5-dichlorophthalic anhydride, there is obtained 0.95 g. of 1,4-dichloro-4-demethoxy-7-desoxydaunomycinone, m.p. 229–231° C.; $[\alpha]_D^{20} = -75°$ (c=0.1 in chloroform). Electronic spectrum: λ max 262, 480, 508 545 nm.

EXAMPLE 5

2,3-dichloro-4-demethoxy-7-desoxydaunomycinone
(III: $R_2=R_3=H$; $R_1=Cl$)

Operating as in Example 3, but employing 4,5-dichlorophthalic anhydride, there are obtained 1.2 g. of 2,3-dichloro-4-demethoxy-7-desoxy-daunomycinone, m.p. 230–232° C.; $[\alpha]_D^{20} = -80°$ (c=0.1 in chloroform). Electronic spectrum: λ max 272, 466, 494, 530 nm.

EXAMPLE 6

1,4-dibromo-4-demethoxy-7-desoxydaunomycinone
(III: $R_1=H$; $R_2=R_3=Br$).

Operating as in Example 4, but employing 3,6-dibromophthalic anhydride, 1,4-dibromo-4-demethoxy-7-desoxydaunomycinone is obtained.

EXAMPLE 7

2,3-dibromo-4-demethoxy-7-desoxydaunomycinone
(III: $R_2=R_3=H$; $R_1=Br$)

Operating as in Example 5, but employing 4,5-dibromophthalic anhydride, 2,3-dibromo-4-demethoxy-7-desoxydaunomycinone is obtained.

Variations and modifications can, of course, be made without departing from the spirit and scope of the invention.

Having described our invention, what we desire to secure by Letters Patent and hereby claim is:

1. A process for preparing an optically active anthracyclinone of the formula III:

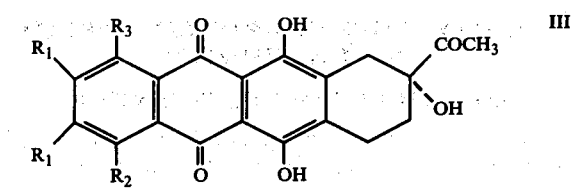

wherein:
(a) $R_1$ is hydrogen and $R_2$ and $R_3$ are the same and are both selected from the group consisting of hydrogen, methyl, methoxy, chlorine and bromine;
(b) $R_2$ and $R_3$ are both hydrogen and $R_1$ is methyl, methoxy, chlorine or bromine; and
(c) $R_1$ and $R_3$ are both hydrogen and $R_2$ is methoxy,
said process comprising melting an optically active (−) 1,4-dimethoxy-6-hydroxy-6-acetyl-tetralin of the formula II:

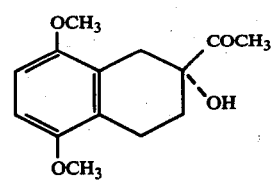

with a phthalic anhydride of the formula IV:

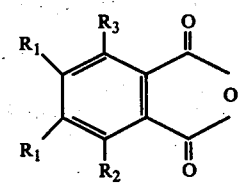

wherein $R_1$, $R_2$ and $R_3$ are as defined above, in the presence of aluminum chloride or bromide and an alkali metal chloride, at a temperature between 130–180° C., for 1 to 10 minutes, to form an anthracyclinone of the formula III, isolating and purifying said anthracyclinone.

2. A process according to claim 1, wherein the alkali metal chloride is LiCl, NaCl or KCl.

3. A process according to claim 1, wherein aluminum chloride and sodium chloride are used in the reaction.

4. 1,4-dimethyl-4demethoxy-7-desoxydaunomycinone.

5. 2,3-dimethyl-4-demethoxy-7-desoxydaunomycinone.

6. 1,4-dichloro-4-demethoxy-7-desoxydaunomycinone.

7. 2,3-dichloro-4-demethoxy-7-desoxydaunomycinone.

8. 1,4-dibromo-4-demethoxy-7-desoxydaunomycinone.

9. 2,3-dibromo-4-demethoxy-7-desoxydaunomycinone.

* * * * *